(12) United States Patent
Kodama et al.

(10) Patent No.: US 7,848,481 B2
(45) Date of Patent: Dec. 7, 2010

(54) X-RAY CT APPARATUS

(75) Inventors: Yuichi Kodama, Hachioji (JP); Ayuta Yamada, Ome (JP); Manabu Noguchi, Tachikawa (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 12/085,869

(22) PCT Filed: Dec. 19, 2006

(86) PCT No.: PCT/JP2006/325690

§ 371 (c)(1),
(2), (4) Date: May 29, 2008

(87) PCT Pub. No.: WO2007/072968

PCT Pub. Date: Jun. 28, 2007

(65) Prior Publication Data

US 2009/0046835 A1 Feb. 19, 2009

(30) Foreign Application Priority Data

Dec. 20, 2005 (JP) .............................. 2005-366958

(51) Int. Cl.
*A61B 6/00* (2006.01)
(52) U.S. Cl. ............................................. 378/15; 378/4
(58) Field of Classification Search ................ 378/4–20, 378/193, 196
See application file for complete search history.

(56) References Cited

U.S. PATENT DOCUMENTS 4,118,629 A * 10/1978 Hounsfield ..................... 378/5
6,956,925 B1 * 10/2005 Hoffman ........................ 378/4
2005/0199059 A1 9/2005 Danz et al.
2006/0222143 A1 * 10/2006 Du .............................. 378/11
2007/0041488 A1 * 2/2007 Hoheisel et al. ................ 378/4

FOREIGN PATENT DOCUMENTS

| JP | 2001-070296 | 3/2001 |
|---|---|---|
| JP | 2004-065477 | 3/2004 |
| JP | 3572191 | 7/2004 |
| JP | 2005-211660 | 8/2005 |
| JP | 2005-270329 | 10/2005 |
| JP | 2006-038836 | 2/2006 |

OTHER PUBLICATIONS

Y. Arai, et al.; "Micro-computed tomography newly developed for in vivo small animal imaging", Oral Radiology, vol. 21, No. 1, 2005.07, pp. 14-18.

* cited by examiner

*Primary Examiner*—Hoon Song
(74) *Attorney, Agent, or Firm*—Jordan and Hamburg LLP (57) ABSTRACT

In an X-ray CT apparatus, an X-ray source and an X-ray detector mounted in a guide arm are freely movable in such a direction as to approach to and separate from a sample. With respect to this movement, the center of gravity of the whole containing respective constituent elements mounted in the guide arm is kept on the rotational axis by a weight balance adjusting mechanism. The weight balance adjusting mechanism contains a movable weight which is freely movable to the guide arm. The movement of the movable weight is controlled so that a difference between the rotational moment around the rotational axis is offset and substantially equal to zero. The moving passage of the movable weight is set on a straight line which is parallel to the moving direction of the X-ray source and the X-ray detector and does not pass through the rotational axis.

3 Claims, 7 Drawing Sheets

Fig. 1A

RELATED ART

Fig. 1B

RELATED ART

X-RAY CT APPARATUS

BACKGROUND OF THE INVENTION

1. Technical Field

The present invention relates to an X-ray CT apparatus, and particularly to an X-ray CT apparatus which is constructed so as to be suitable for an industrial application.

2. Background Art

An X-ray CT (computed tomography) apparatus is an apparatus for detecting X-rays transmitted through an object from various positions/directions and determining a density distribution of an X-ray transmitted cross-section by numerical calculation, thereby imaging the density distribution of the cross-section. The X-ray CT apparatus is mainly used in a medical diagnosis field. Research and development on medical X-ray CT apparatuses targeting human bodies as test objects have been promoted, and various kinds of medical X-ray CT apparatuses having excellent functions have been proposed at present.

Furthermore, in the industrial field, X-ray CT apparatuses are used for nondestructive inspection of metal materials, internal inspection of packages, etc. However, as compared with the medical X-ray CT apparatuses, the number of development proposals of industrial X-ray CT apparatuses is smaller. Through the investigation result of this applicant, many patent documents concerning medical X-ray CT apparatuses have been found, however, only Patent Document 1 concerning an industrial X-ray CT apparatus has been found.

Figure 1A:
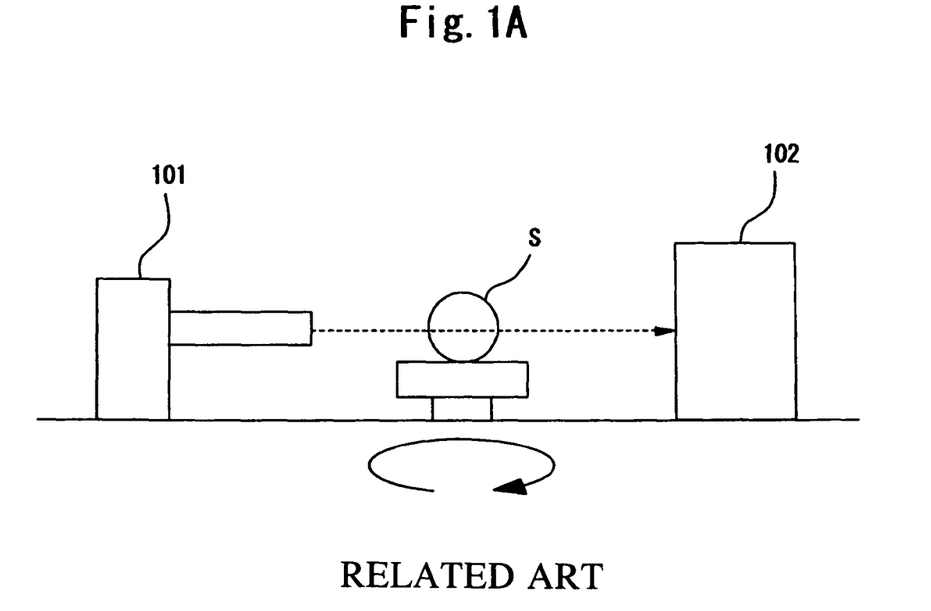
FIGS. 1A and 1B are diagrams showing a conventional X-ray CT apparatus.

In general, the industrial X-ray CT apparatus is designed so that an X-ray source 101 and an X-ray detector 102 are fixed so as to face each other as shown in FIG. 1A, a test object (sample) S is disposed at the intermediate portion therebetween, and also the test object S is rotated. Even in this construction, when the test object is solid such as a metal material, a package or the like, it can be freely rotated and thus there is no obstruction. However, the application of the industrial X-ray CT apparatus has been recently broadened, and the applicant has had a requirement of obtaining CT images of those objects which have not been hitherto expected as test objects, such as materials having fluidity such as liquid, and small animals which are not suitable for rotational operation.

The present invention has been implemented in order to meet the requirement as described above, and has an object to provide an X-ray CT apparatus that can obtain proper CT images of various objects without rotating test objects (samples) and is suitable for industrial applications.

Furthermore, the present invention has an object to provide an X-ray CT apparatus in which imaging magnification and resolution (that is, imaging area (FOV, Field of View) can be easily changed.

SUMMARY OF THE INVENTION

In order to attain the above object, according to the present invention, an X-ray CT apparatus comprises an X-ray source for generating X-ray, sample holding means for holding a sample, an X-ray detector for detecting X-ray emitted from the X-ray source and transmitted through the sample, and a rotational support member in which the X-ray source and the X-ray detector are mounted, and the following conditions (a) to (h) are satisfied:

(a) the rotational support member has an open space surrounding a sample held by the sample holding means;

(b) the rotational support member is freely rotatable around an axis passing through the sample held by the sample holding means;

(c) the rotational support member has the X-ray source and the X-ray detector mounted therein so that the X-ray source and the X-ray detector face each other so as to sandwich the sample held by the sample holding means between the X-ray source and the X-ray detector;

(d) the rotational support member can move one or both of the X-ray source and the X-ray detector so that one or both of the X-ray source and the X-ray detector approach to or separate from the sample held by the sample holding means;

(e) the rotational support member is designed so that the center of gravity of the whole containing all constituent elements mounted in the rotational support member is set on the rotational axis of the rotational support member;

(f) the rotational support member is equipped with weight balance adjusting means for keeping the center of gravity of the whole containing all the constituent elements mounted in the rotational support member on the rotational axis of the rotational support member with respect to the movement of one or both of the X-ray source and the X-ray detector in the approach/separation direction to/from the sample;

(g) the weight balance adjusting means contains a movable weight that is mounted to be freely movable to the rotating support member, and the movement of the movable weight is controlled so that a difference between rotational moment around the rotational axis of the rotational support member is offset and substantially equal to zero; and (h) the movable weight has a moving passage set on a straight line which is parallel to the moving direction of the X-ray source or the X-ray detector and does not pass through the rotational axis of the rotational support member.

As described above, the X-ray CT apparatus is configured so that the rotational support member is freely rotatable around the axis passing through the sample held by the sample holding means, whereby the entire periphery of the sample can be scanned without rotating the sample. As a result, proper X-ray CT imaging can be implemented without trouble with respect to samples which have not been hitherto expected such as materials having fluidity such as liquid, and small animals which are not suitable for rotational operation.

In addition, in the X-ray CT apparatus, the rotational support member is configured so that one or both of the X-ray source and the X-ray detector is movable in such a direction as to approach to and separate from the sample held by the sample holding means, whereby one or both of the distance between the X-ray source and the sample and the distance between the sample and the X-ray detector can be freely adjusted. As a result, the imaging magnification and the resolution (that is, the imaging area) can be easily changed.

Here, the rotational support member may comprise a guide arm that is freely rotatable around an axis passing through the sample, and an X-ray source holding stage that holds the X-ray source and is freely movable on the guide arms in such a direction as to approach to and separate from the sample.

Furthermore, the rotational support member may contain an X-ray detector holding stage that holds the X-ray detector and is freely movable on the guide arm in such a direction as to approach to and separate from the sample.

Many conventional medical X-ray CT apparatuses are designed so that an X-ray source and an X-ray detector are contained in a cylindrical gantry (Gantry) and a human body as a test object is inserted in the gantry to implement X-ray CT imaging. If this type of medical X-ray CT apparatus is industrially applied, it is difficult to position a sample because the holding position of the sample (test object) is in a closed space covered by the gantry. Furthermore, it is also difficult in the X-ray CT apparatus to secure a space in which structures for applying external force to a sample, applying a voltage to the sample, changing the temperature of the sample and setting the surrounding atmosphere of the sample to vacuum or any gas atmosphere are mounted.

Figure 1B:
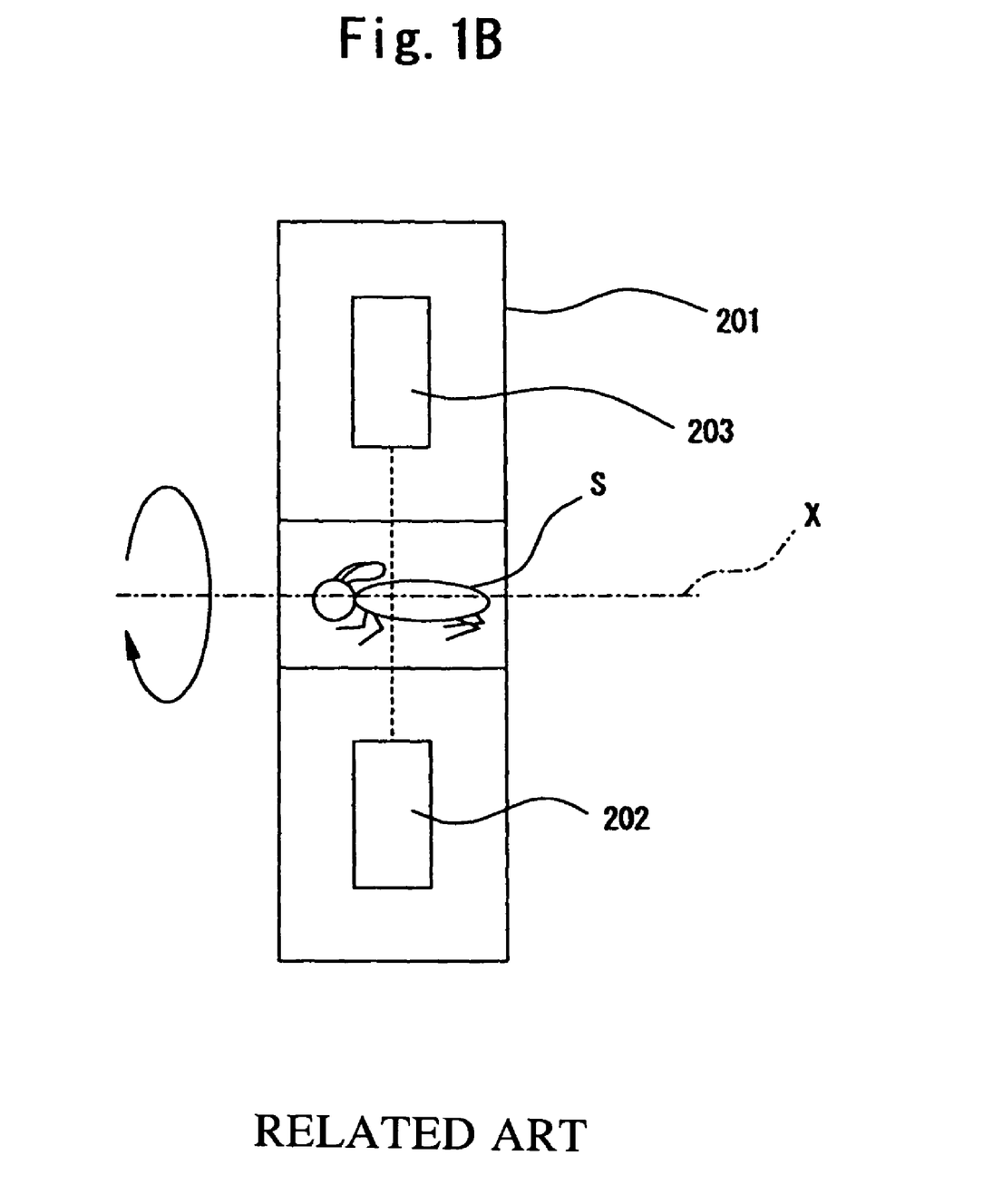

Still furthermore, a compact X-ray CT apparatus designed as shown in FIG. 1B is sold as an apparatus for diagnosing small animals in the market. In the compact X-ray CT apparatus shown in FIG. 1B, an X-ray source 202 and an X-ray detector 203 are disposed so as to face each other in a cylindrical gantry 201, and the gantry 201 is rotated around the center axis X.

In this type of X-ray CT apparatus, the holding position of a small animal (test object) is in a closed space covered by the gantry, and thus it is difficult to position the sample.

In addition, the surrounding of the test object is blocked by the gantry 201, and thus this X-ray CT apparatus cannot be used in such a specific application that CT imaging is fitly carried out on a small animal during an operation of the small animal.

Figure 2:
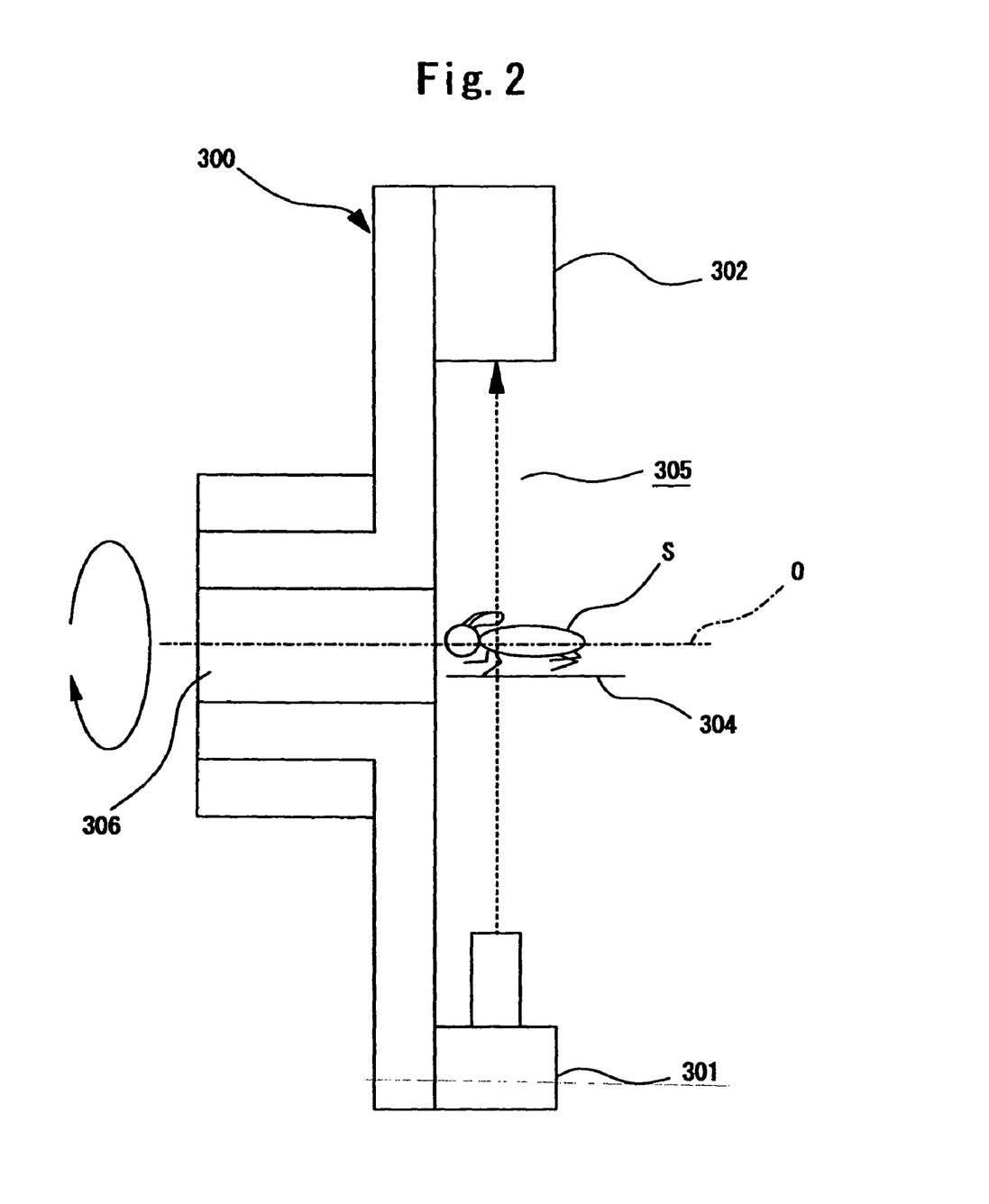
FIG. 2 is a diagram showing the feature of an X-ray CT apparatus of the present invention.

On the other hand, in the construction of the present invention, a rotational support member (guide arm) 300 has an X-ray source 301 and an X-ray detector 302 mounted therein as shown in FIG. 2. The rotational support member 300 forms an open space 305 at the surrounding of the sample (test object) S held by a sample holding means 304. The rotational support member 300 is rotated around a rotational axis O, and thus the positioning of the sample is facilitated, so that the workability is enhanced. Furthermore, a structure of applying a voltage to the sample, a structure of heating or cooling the sample, a structure of setting the surrounding atmosphere of the sample to vacuum or any gas atmosphere, etc. can be set in the X-ray CT apparatus, so that the application range of the X-ray CT imaging can be drastically broadened. Various kinds of options used for X-ray diffraction apparatuses can be used as these types of additional structures.

Furthermore, the X-ray CT apparatus can be also used in such a special application that a small animal is fitly subjected to CT examination during an operation of the small animal, and satisfies various requirements from users.

The rotational support member is preferably designed so that the center of gravity of the whole containing all constituent elements mounted in the rotational support member is disposed on the rotational axis to keep the weight balance fair.

If the weight balance is not proper, an eccentric torque acts on the rotational support member, and thus there is a risk that the rotational motion is not smoothly made or deflection occurs in the rotational support member.

Therefore, according to the present invention, there is provided the weight balance adjusting means for keeping the center of gravity of the whole on the rotational axis with respect to the movement of one or both of the X-ray source and the X-ray detector in such a direction as to approach to and separate from the sample. Therefore, the X-ray CT apparatus can dispose the center of gravity of the whole on the rotational axis even when the X-ray source or the X-ray detector is moved, and the proper weight balance can be structurally kept.

The weight balance adjusting means contains a movable weight which is mounted so as to be freely movable to the rotational support member, and controls the movement of the movable weight so that a difference between rotational moment around the rotational axis is offset and substantially equal to zero.

Here, the moving passage of the movable weight is set on a straight line which is parallel to the moving direction of the X-ray source or the X-ray detector and does not pass through the rotational axis of the rotational support member.

When the moving passage of the movable weight is disposed on the moving passage of the X-ray source or the X-ray detector, a complicated structure design is required to the X-ray CT apparatus because the interference between the movable weight and the X-ray source or the X-ray detector must be avoided. Furthermore, it is also difficult to approach the moving passage of the movable weight to the neighborhood of the rotational axis of the rotational support member because the sample is disposed on the rotational axis of the rotational support member. Accordingly, in the X-ray CT apparatus, the moving passage of the movable weight must be provided at a position which is greatly away from the rotational axis, and thus the rotational support member must be designed in a large size.

According to the present invention, the moving passage of the movable weight is set on a straight line which is parallel to the moving direction of the X-ray source or the X-ray detector and does not pass through the rotational axis of the rotational support member as described above, so that it is unnecessary to require a complicated structure design and thus the rotational support member can be miniaturized.

A fixed weight is mounted separately from the movable position in the rotational support member, and the rotational moment acting on the basis of the distance from the rotational axis to the moving passage of the movable weight and the weight of the movable weight is offset by the fixed weight.

As described above, according to the present invention, the X-ray CT apparatus is designed so that the rotational support member is freely rotatable around the axis passing through the sample held by the sample holding means, whereby the entire periphery of the sample can be scanned without rotating the sample. As a result, the X-ray CT apparatus can implement the proper X-ray CT imaging, without trouble, on samples which have not been hitherto expected, such as materials having fluidity such as liquid, and small animals which are not suitable for the rotational operation.

In addition, in the X-ray CT apparatus, the rotational support member is designed so that one or both of the X-ray source and the X-ray detector is movable in such a direction as to approach to and separate from the sample held by the sample holding means, whereby one or both of the distance between the X-ray source and the sample and the distance between the sample and the X-ray detector can be arbitrarily adjusted. As a result, the imaging magnification and the resolution (that is, the imaging area) can be easily changed.

Furthermore, the X-ray CT apparatus is configured so that one or both of the X-ray source and the X-ray detector is moved in such a direction as to approach to and separate from the sample and the whole center of gravity is kept on the rotational axis, whereby the center of gravity of the whole can be disposed on the rotational axis even when the X-ray source or the X-ray detector is disposed on the rotational axis, and the proper structural weight balance can be kept.

DETAILED DESCRIPTION OF THE INVENTION

An embodiment of the present invention will be described hereunder in detail with reference to the drawings.

Figure 3:
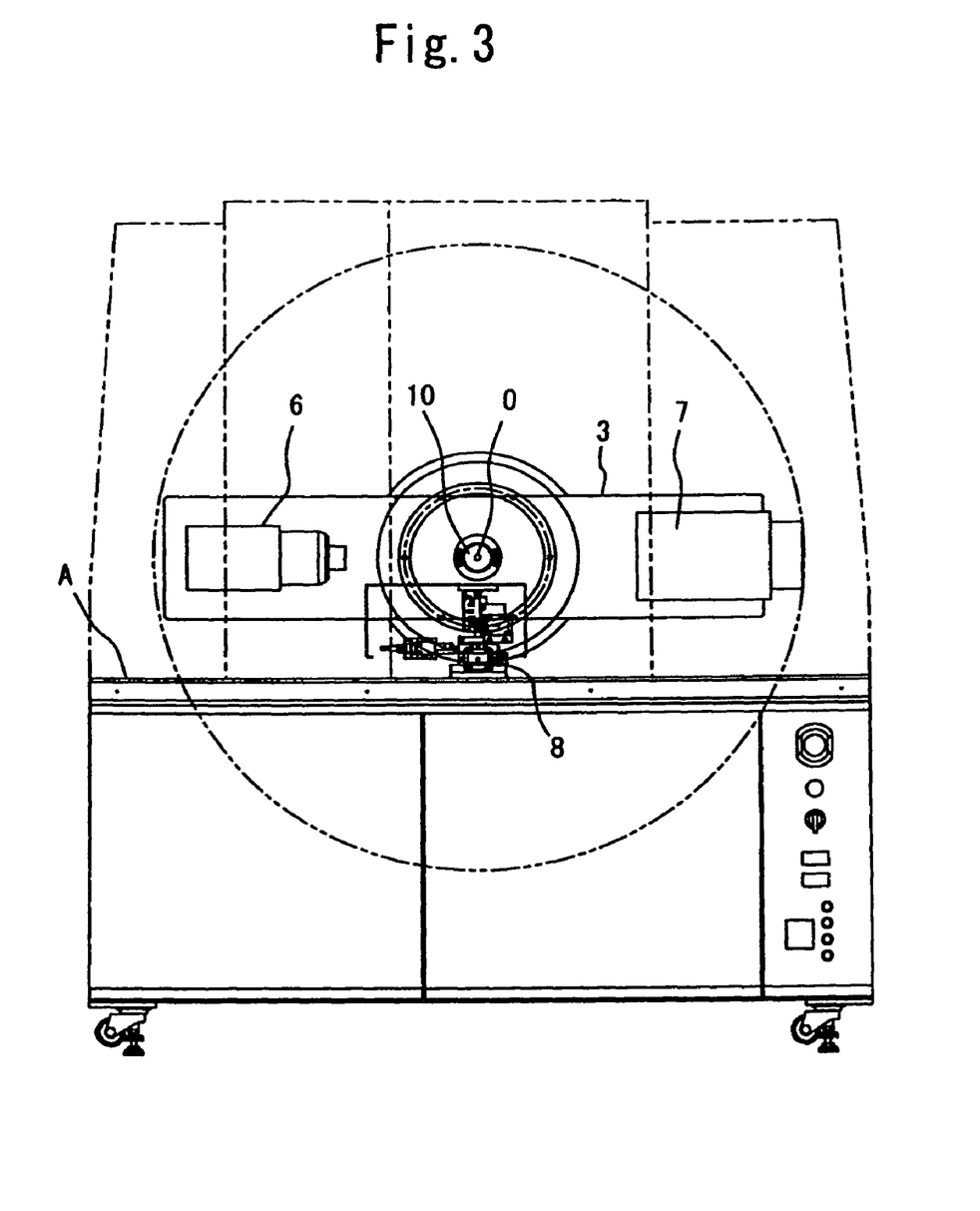
FIG. 3 is a front view showing the X-ray CT apparatus according to an embodiment of the present invention.
Figure 4:
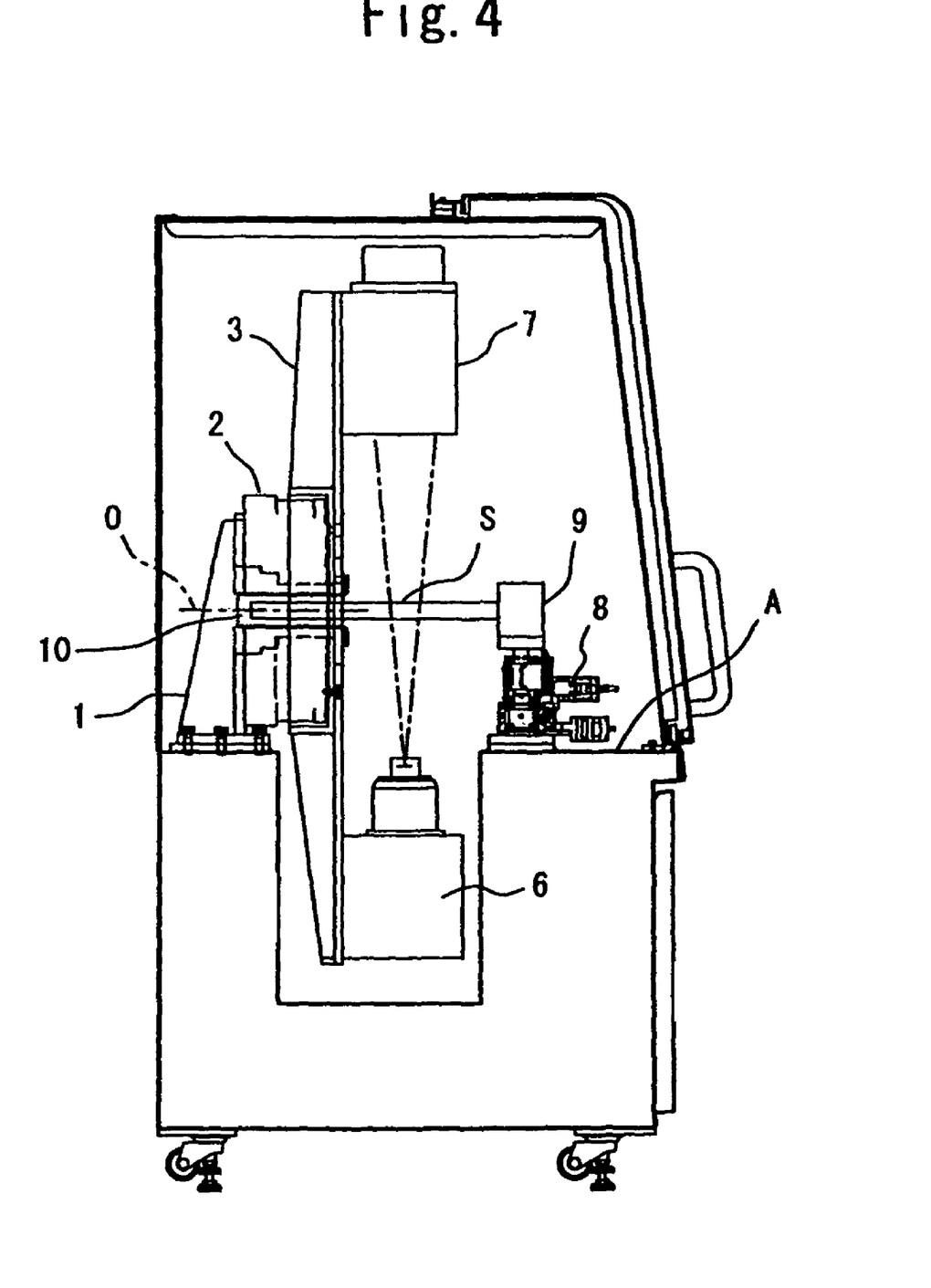
FIG. 4 is a side perspective view showing of the X-ray CT apparatus according to the embodiment of the present invention.

FIG. 3 is a front view showing an X-ray CT apparatus according to an embodiment of the present invention, and FIG. 4 is a side perspective view showing the X-ray CT apparatus. First, the overall construction of the X-ray CT apparatus according to the embodiment will be described with reference to these drawings.

As shown in FIG. 4, a bearing stand 1 is mounted at a position near to the rear portion of the top surface of a table A of the main body of the X-ray CT apparatus. The bearing stand 1 is provided with a cylindrical bearing 2, and the center portion of a guide arm 3 (rotational support member) is freely rotatably mounted to the bearing 2. Here, the center axis of the bearing 2 corresponds to a rotational axis O of the guide arm 3, and the rotational axis O extends in the horizontal direction. A sample S is disposed on the rotational axis O (horizontal axis).

As shown in FIG. 3, the guide arm 3 is formed in an elongated shape which extends in the longitudinal direction with the rotational axis set as the center of the guide arm 3. An X-ray source 6 and an X-ray detector 7 are mounted in the guide arm 3 so as to sandwich the rotational axis O therebetween. The X-ray source 6 and the X-ray detector 7 are freely movable independently of each other in such a direction as to approach to and separate from the rotational axis O.

In the X-ray CT apparatus, the magnification and the resolution of the X-ray CT apparatus, the resolution on the sample S and the field of view can be arbitrarily changed by changing the distance between the X-ray source 6, the X-ray detector 7 and the sample S.

As shown in FIG. 4, a sample holding stand 8 is disposed at a position near to the front portion of the top surface of the table A of the main body of the apparatus. Each kind of sample holders 9 corresponding to the property, etc. of the sample S is mounted at the upper portion of the sample holding stand 8. For example, in the case of a rod-like sample S as shown in FIG. 4, a sample holder having a chuck for pinching one end of the sample is preferably used, and in the case of a liquid sample S, a sample holder having a container in which the liquid sample S is inserted and held is preferably used.

The sample holding stand 8 and the sample holder 9 constitute a sample holding means for holding the sample S, and by the sample holding means, the sample S is disposed at the position at which an X-ray radiated from the X-ray detector 7 and the rotational axis O intersect to each other.

As described above, in the X-ray CT apparatus of this embodiment in which the X-ray source 6 and the X-ray detector 7 are mounted on the surface of the guide arm 3, the surrounding of the sample S held by the sample holder 9 is set to an open space, and thus the sample S is easily positioned, so that the workability is enhanced. In addition, the sample S can be easily operated during CT imaging operation (for example, during the operation of a small animal). Furthermore, in the X-ray CT apparatus, the rotational axis O is set in the horizontal direction. Accordingly, images of the cross-sections of the sample S can be picked up while the sample S is held in a horizontal position, and the X-ray CT apparatus is suitably used for CT imaging of samples which are difficult to be disposed in a vertical position or tilted position, such as small animals, samples having fluidity. In addition, the rotational orbit of the guide arm 3 does not have planar spread, and thus space can be saved.

As shown in FIG. 4, a through hole 10 (transmission space) is formed along the rotational axis O at the rotational axis O portion of the bearing 2 and the guide arm 3. The through hole 10 can be used as an arrangement space of the sample S, and for example a rod-like sample S can be held without trouble by disposing a part of the rod-like sample S in the through hole 10 (see FIG. 4).

The guide arm 3 described above is adjusted so that the center of gravity of the whole containing the constituent elements (the X-ray source 6, the X-ray detector 7, etc.) mounted in the guide arm 3 is located on the rotational axis O. By adjusting the center-of-gravity position as described above, an eccentric torque is prevented from acting on the guide arm 3, and thus the guide arm 3 can be smoothly rotated in the X-ray CT apparatus.

Figure 5:
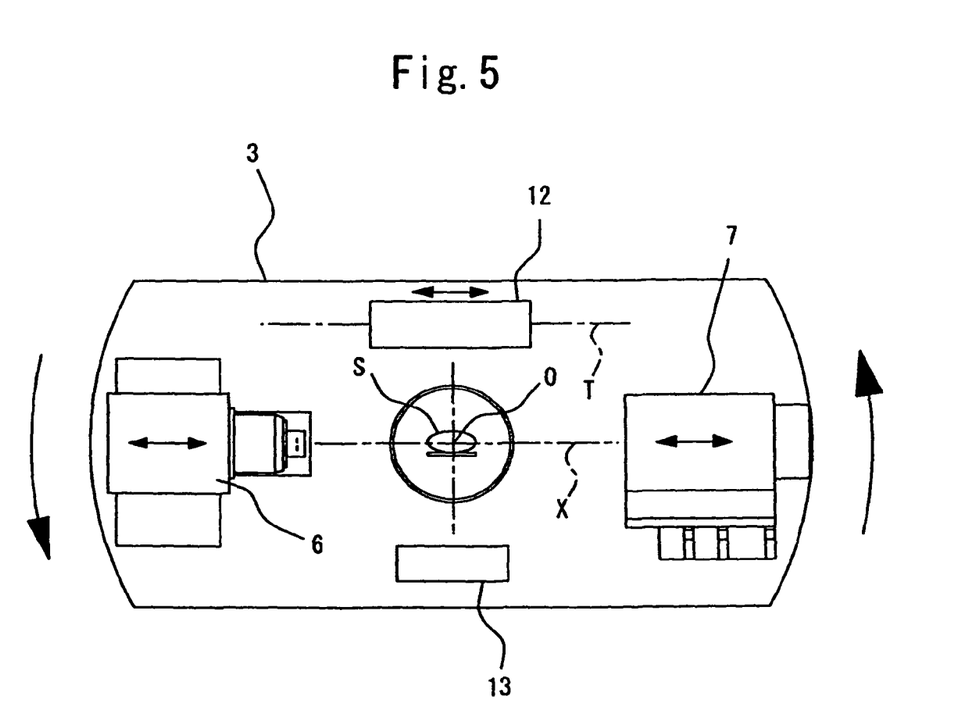
FIG. 5 is a diagram showing the construction of a guide arm and a weight balance adjusting mechanism.

Furthermore, in this embodiment, the X-ray source 6 and the X-ray detector 7 are movable, and the weight balance adjusting mechanism (weight balance adjusting mechanism) for automatically adjusting the weight balance in connection with the movement of the X-ray source 6 and the X-ray detector 7 is installed in the X-ray CT apparatus. FIG. 5 is a diagram showing the construction of the weight balance adjusting mechanism according to this embodiment.

The weight balance adjusting mechanism comprises a movable weight 12 which is freely movable on the guide arm 3, and a fixed weight 13 fixed onto the guide arm 3. Here, the movable weight 12 is freely movable along a moving passage T which is parallel to the moving direction of the X-ray source 6 and the X-ray detector 7 and does not pass through the rotational axis O of the guide arm 3. The X-ray source 6 and the X-ray detector 7 are freely movable along the X-axis passing through the rotational axis O, and the moving passage T is parallel to the X-axis.

In the X-ray CT apparatus, the weight balance of the guide arm 3 can be easily adjusted irrespective of the distance between the movable weight 12 and the rotational axis O by setting the moving passage of the movable weight 12 in parallel to the moving direction of the X-ray source 6 and the X-ray detector 7.

As described above, according to the construction of this embodiment, the imaging magnification and the resolution (that is, the imaging area) can be changed in a broad range by only the moving mechanism of one movable weight 12 while the sample S is kept stationary in a horizontal position.

Furthermore, in the X-ray CT apparatus, the moving passage of the movable weight 12 is set not to pass through the rotational axis O, so that the distance to the rotational axis O can be shortened and the guide arm 3 can be miniaturized.

Separately from the movable weight 12, the fixed weight 13 is mounted in the guide arm 3, and the rotational moment acting on the basis of the distance from the rotational axis O to the moving passage of the movable weight 12 and the weight of the movable weight 2 is offset by the fixed weight 13.

Figure 6:
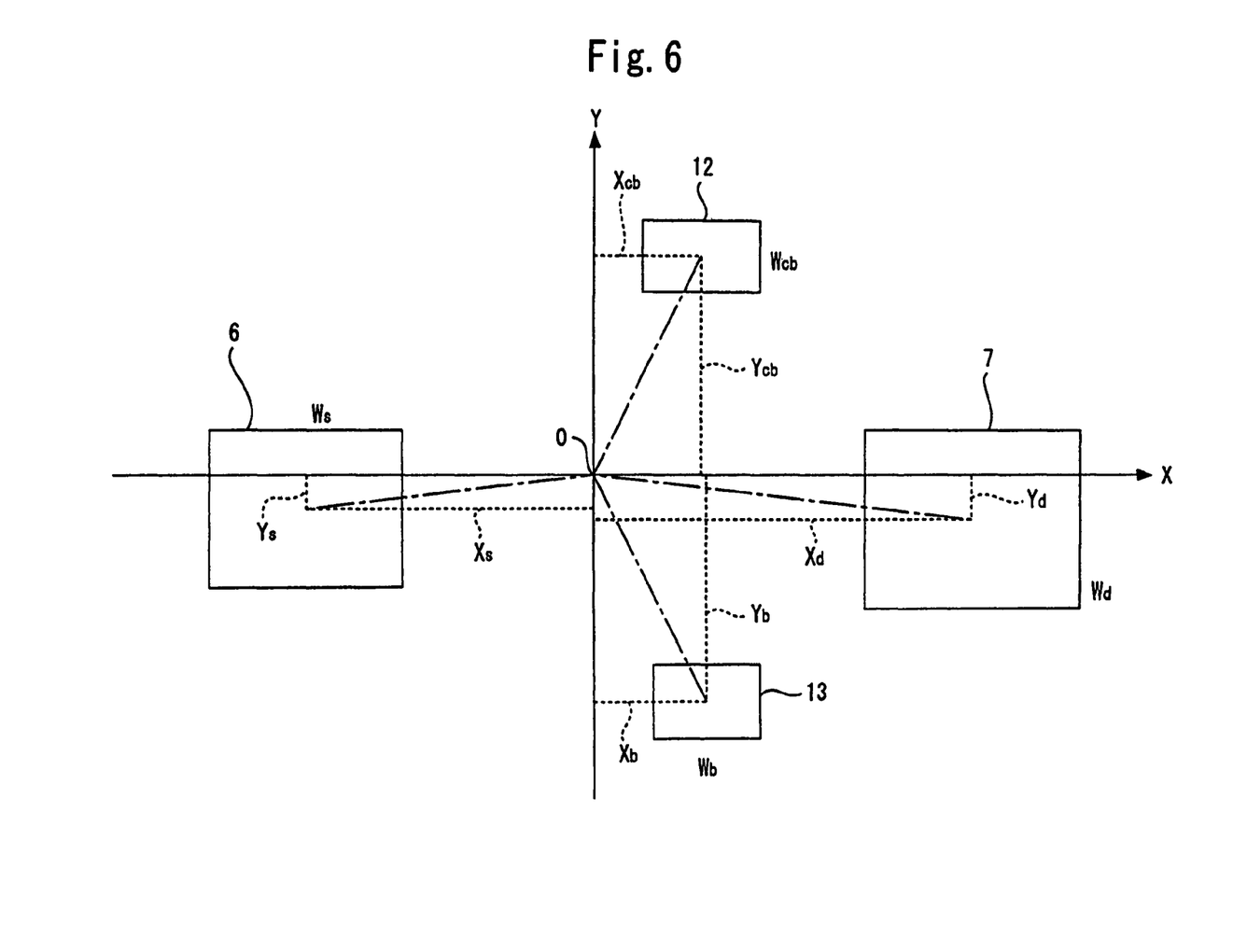
FIG. 6 is a diagram showing the setting of the weight balance adjusting mechanism.

Here, there is considered an XY coordinate system which contains the rotational axis O as the origin and comprises an X-axis parallel to the X-ray source 6 and the X-ray detector 7 and a Y-axis vertical to the X-axis as shown in FIG. 6. For convenience of description, it is assumed that the center of gravity of the guide arm 3 is made coincident with the rotational axis O.

In this XY coordinate system, the Y-axis components of the rotational moment around the rotational axis O for the respective constituent elements mounted in the guide arm 3 are as follows.

(1) The Y-axis component of the rotational moment of the fixed weight 13 is Wb·Yb.

(2) The Y-axis component of the rotational moment of the movable weight 12 is Wcb·Ycb.

(3) The Y-axis component of the rotational moment of the X-ray source 6 is Ws·Ys.

(4) The Y-axis component of the rotational moment of the X-ray detector 7 is Wd·Yd.

With respect to the fixed weight 13, the distance Yb between the weight Wb and the X-axis is adjusted so that differences between the Y-axis components of the rotational moments are equal to zero.

Next, moving control of the movable weight 12 will be described.

In the XY coordinate system shown in FIG. 6, the X-axis components of the rotational moment around the rotational axis O for the respective constituent elements mounted in the guide arm 3 are as follows.

(1) The X-axis component of the rotational moment of the movable weight 12 is Wcb·Xcb.

(2) The X-axis component of the rotational moment of the fixed weight 13 is Wb·Xb.

(3) The X-axis component of the rotational moment of the X-ray source 6 is Ws·Xs.

(4) The X-axis component of the rotational moment of the X-ray detector 7 is Wd·Xd.

The position Xcb of the movable weight 12 on the moving passage T is automatically adjusted so that differences between the X-axis components of the rotational moments are equal to zero (that is, so as to satisfy the following equation).

$$Xcb=(Wb\cdot Xb+Ws\cdot Xs+Wd\cdot Xd)/Wcb$$

The present invention is not limited to the above embodiment.

For example, the X-ray CT apparatus of the present invention is suitably used in the industrial application, however, it may be used in other applications than the industry, for example, experiments and researches in medical diagnosis and other fields.

The X-ray CT apparatus may be designed so that any one of the X-ray source 6 and the X-ray detector 7 is fixed to a predetermined position on the guide arm 3.

Furthermore, in the above embodiment, the center of gravity of the guide arm 3 is made coincident with the rotational axis O. However, if the center of gravity is away from the rotational axis O, the rotational moment of the guide arm 3 must be considered when the fixed weight 13 is adjusted or the movement of the movable weight 12 is controlled.

As described above, according to the present invention, the X-ray CT apparatus is designed so that the rotational support member is freely rotatable around the axis passing through the sample held by the sample holding means, whereby the overall periphery of the sample can be scanned without rotating the sample. As a result, the X-ray CT apparatus can implement the proper X-ray CT imaging, without trouble, on samples which have not been hitherto expected such as materials having fluidity such as liquid, and small animals which are not suitable for rotational operation.

In addition, the rotational support member of the X-ray CT apparatus is designed so that one or both of the X-ray source and the X-ray detector is movable in such a direction as to approach to or separate from the sample held by the sample holding means, whereby one or both of the distance between the X-ray source and the sample and the distance between the sample and the X-ray detector can be freely adjusted. As a result, the imaging magnification and the resolution (that is, the imaging area) can be easily changed.

Furthermore, the X-ray CT apparatus is designed so that the overall center of gravity thereof is kept on the rotational axis with respect to the movement of one or both of the X-ray source and the X-ray detector in such a direction as to approach to and separate from the sample, whereby the overall center of gravity can be easily located on the rotational axis even when the X-ray source or the X-ray detector is moved, so that the proper structural weight balance can be maintained.

The invention claimed is:

1. A non-gantry type X-ray CT apparatus comprising:
   an upright stand configured to be mounted on a support surface therefor;
   a bearing member supported on the stand;
   a rotational support member that is a single arm that is mounted with the bearing member for rotational movement relative thereto, the single arm defining a center longitudinal axis and comprising a pair of longitudinal end portions between which the single arm extends;
   an X-ray source for generating an X-ray;
   a sample holding means for holding a sample; and
   an X-ray detector for detecting an X-ray emitted from the X-ray source and transmitted through the sample, the X-ray source and the X-ray detector each being mounted on the rotational support member at a respective longitudinal end portion thereof, the rotational support member further comprising a weight balance adjusting means so that:
   (a) the rotational support member has an open space surrounding a sample held by the sample holding means;
   (b) the rotational support member is freely rotatable around an axis passing through the sample held by the sample holding means;
   (c) the X-ray source and the X-ray detector are disposed so as to face each other through the sample held by the sample holding means;
   (d) one or both of the X-ray source and the X-ray detector can move along an axis in a radial direction which passes through the rotational axis of the rotational support member, said axis being the center longitudinal axis of the rotational support member along which the X-ray source and the X-ray detector are movable so as to approach and separate from one another and the sample held by the sample holding means;
   (e) the center of gravity of the rotational support member is coincident with the rotational axis of the rotational support member;
   (f) the rotational support member comprises a weight balance adjusting means for automatically keeping the center of gravity thereof coincident with the rotational axis of the rotational support member upon movement of one or both of the X-ray source and the X-ray detector in the approach/separation direction to/from each other and the sample along the center longitudinal axis of the rotational support member;
   (g) the weight balance adjusting means contains only one movable weight and only one fixed weight each being positioned on opposite sides of the center longitudinal axis of the rotational support member, the movable weight being mounted to be freely movable on the rotational support member, the movement of the movable weight being controlled to move so that a difference between components of the rotational moment around the rotational axis of the rotational support member is offset and substantially equal to zero as a result of automatic movement of the movable weight which is actuated by at least longitudinal movement of one or both of the X-ray source and the X-ray detector along the center longitudinal axis of the rotational support member; and (h) the movable weight comprises a moving passage set only on a straight line for movement therealong and which is parallel to the moving direction of the X-ray source and the X-ray detector along the center longitudinal axis of the rotational support member so as to not pass through the rotational axis of the rotational support member.

2. The X-ray CT apparatus according to claim 1, wherein the fixed weight offsets a rotational moment based on the distance from the rotational axis of the rotational support member to the moving passage of the movable weight and the weight of the movable weight.

3. A non-gantry type X-ray CT apparatus comprising:
an upright stand;
a bearing supported on the stand;
a rotational support member that is a single arm that is mounted with the bearing member for rotational movement relative thereto, the single arm defining a center longitudinal axis and comprising a pair of longitudinal end portions between which the single arm extends;
an X-ray source for generating an X-ray;
a sample holding means for holding a sample; and
an X-ray detector for detecting an X-ray emitted from the X-ray source and transmitted through the sample, the X-ray source and the X-ray detector each being mounted on the rotational support member at a respective longitudinal end portion thereof, the rotational support member further comprising a weight balance adjusting means so that:

(a) the rotational support member has an open space surrounding a sample held by the sample holding means;

(b) the rotational support member is freely rotatable around an axis passing through the sample held by the sample holding means;

(c) the X-ray source and the X-ray detector are disposed so as to face each other through the sample held by the sample holding means;

(d) one or both of the X-ray source and the X-ray detector can move along an axis in a radial direction which passes through the rotational axis of the rotational support member, said axis being the center longitudinal axis of the rotational support member along which the X-ray source and the X-ray detector are movable so as to approach and separate from one another and the sample held by the sample holding means;

(e) the center of gravity of the rotational support member is coincident with the rotational axis of the rotational support member;

(f) the rotational support member comprises a weight balance adjusting means for automatically keeping the center of gravity thereof coincident with the rotational axis of the rotational support member upon movement of one or both of the X-ray source and the X-ray detector in the approach/separation direction to/from each other and the sample along the center longitudinal axis of the rotational support member;

(g) the weight balance adjusting means contains only one movable weight and only one fixed weight each being positioned on opposite sides of the center longitudinal axis of the rotational support member, the movable weight being mounted to be freely movable on the rotational support member, the movement of the movable weight being controlled to move so that a difference between components of the rotational moment around the rotational axis of the rotational support member is offset and substantially equal to zero as a result of automatic movement of the movable weight which is actuated by at least longitudinal movement of one or both of the X-ray source and the X-ray detector along the center longitudinal axis of the rotational support member;

(h) the movable weight comprises a moving passage set only on a straight line for movement therealong and which is parallel to the moving direction of the X-ray source and the X-ray detector along the center longitudinal axis of the rotational support member so as to not pass through the rotational axis of the rotational support member; and (i) the offset and zero sum corresponding to the controlled movement of the movable weight are obtained, with respect to an x-y coordinate system, insofar as (1) Wcb is the weight of the movable weight,
(2) Wb is the weight of the fixed weight,
(3) the X-axis component of the rotational moment of the movable weight is Wcb·Xcb,
(4) the X-axis component of the rotational moment of the fixed weight is Wb·Xb,
(5) the X-axis component of the rotational moment of the X-ray source is Ws·Xs, and
(6) the X-axis component of the rotational moment of the X-ray detector is Wd·Xd, so that Xcb=(Wb·Xb+Ws·Xs+Wd·Xd)/Wcb.

* * * * *